United States Patent
Piraube

(10) Patent No.: US 11,150,491 B2
(45) Date of Patent: Oct. 19, 2021

(54) DISTRIBUTED OPTICAL JOB AND MANUFACTURING COMPUTATION SYSTEMS AND METHODS

(71) Applicant: Essilor International, Charenton-le-Pont (FR)

(72) Inventor: Sebastien Piraube, Dallas, TX (US)

(73) Assignee: Essilor International, Charenton-le-Pont (FR)

( * ) Notice: Subject to any disclaimer, the term of this patent is extended or adjusted under 35 U.S.C. 154(b) by 246 days.

(21) Appl. No.: 16/061,746

(22) PCT Filed: Dec. 17, 2015

(86) PCT No.: PCT/EP2015/080177
§ 371 (c)(1),
(2) Date: Jun. 13, 2018

(87) PCT Pub. No.: WO2017/102003
PCT Pub. Date: Jun. 22, 2017

(65) Prior Publication Data
US 2018/0364498 A1    Dec. 20, 2018

(51) Int. Cl.
*G02C 7/02* (2006.01)
*G16H 40/20* (2018.01)
*G16H 10/40* (2018.01)
*G16H 10/60* (2018.01)
*G06Q 50/00* (2012.01)

(52) U.S. Cl.
CPC ............. *G02C 7/027* (2013.01); *G06Q 50/00* (2013.01); *G16H 10/40* (2018.01); *G16H 10/60* (2018.01); *G16H 40/20* (2018.01)

(58) Field of Classification Search
CPC ........ G02C 7/027; G16H 40/20; G16H 10/40; G16H 10/60; G06Q 50/00
See application file for complete search history.

(56) References Cited

U.S. PATENT DOCUMENTS

2008/0033836 A1* 2/2008 Shinohara .......... G06Q 30/0603
705/26.81
2009/0276238 A1* 11/2009 Filipovich .............. G06Q 10/10
705/2

(Continued)

FOREIGN PATENT DOCUMENTS

CN      105026989 A    11/2015

OTHER PUBLICATIONS

International Search Report dated Apr. 25, 2016, in PCT/EP2015/080177, filed Dec. 17, 2015.

*Primary Examiner* — Sujay Koneru
(74) *Attorney, Agent, or Firm* — Oblon, McClelland, Maier & Neustadt, L.L.P.

(57) ABSTRACT

Systems, computer-implemented methods, and computer-readable storage media that execute, are configured to execute, or store instructions that enable modification of optical manufacturing data, including a computer-implemented method for modifying optical manufacturing data. The method includes receiving the optical manufacturing data associated with an optical job and modifying the optical manufacturing data using manufacturing logic to generate modified optical manufacturing data. The modified optical manufacturing data is then used in the manufacturing process of the optical job.

14 Claims, 8 Drawing Sheets

(56) References Cited

U.S. PATENT DOCUMENTS

| | | | | |
|---|---|---|---|---|
| 2010/0228375 A1* | 9/2010 | Brechemier | ............ | B24B 9/146 |
| | | | | 700/110 |
| 2011/0257930 A1* | 10/2011 | Gourraud | ......... | B29D 11/00009 |
| | | | | 702/150 |
| 2014/0302749 A1* | 10/2014 | Samukawa | ............ | G05B 19/19 |
| | | | | 451/5 |
| 2015/0055085 A1* | 2/2015 | Fonte | .................... | H04L 65/403 |
| | | | | 351/178 |
| 2016/0011437 A1* | 1/2016 | Nishimura | ............. | G02C 7/027 |
| | | | | 351/204 |
| 2016/0026001 A1 | 1/2016 | Nishimura et al. | | |
| 2016/0349535 A1* | 12/2016 | Creighton | ........ | B29D 11/00086 |

* cited by examiner

DISTRIBUTED OPTICAL JOB AND MANUFACTURING COMPUTATION SYSTEMS AND METHODS

BACKGROUND

The present disclosure relates generally to the field of optical lab information technology systems, equipment, and optical/manufacturing data calculation systems and methods.

Optical lens design is the process of designing a lens to meet a set of performance requirements and constraints such as, but not limited to, cost and manufacturing limitations. Parameters include surface profile types (spherical, aspheric, holographic, diffractive, etc.), as well as radius of curvature, distance to the next surface, material type, and optionally tilt and decenter values. The process is computationally intensive, using ray tracing or other techniques to model how the lens affects light that passes through it.

Thus, calculation systems, also known as Lens Design Systems (LDS), are generally centralized, either on servers (in the lab, or in a server farm), or on web-services. The LDS performs the calculations and sends the data required to manufacture the lens in the lab to a Lab Management System (LMS) that controls the processes and equipment within an optical manufacturing lab (Rx lab). However, this forces the LDS to have knowledge of every piece of equipment and its configuration within the optical manufacturing lab in order to provide the manufacturing data back to the LMS. Thus, in order to deploy new products or new manufacturing processes today, the equipment manufacturers and the design vendors must work with the LMS companies to have them update the software in order to integrate the new products, equipment or processes. This requires months of negotiation, specification, and development cycle. The result is that the time to market of new products and new manufacturing processes (new equipment, new process, new data) is impacted by making the deployment phase to the Rx lab really challenging.

Accordingly, the present application seeks to provide systems and methods for improving one or more problems associated with current systems and processes.

BRIEF SUMMARY OF THE DISCLOSED EMBODIMENTS

The disclosed embodiments include systems, computer-implemented methods, and computer-readable storage media that execute, are configured to execute, or store instructions that enable the modification of optical manufacturing data.

As one example, specific embodiments disclosed herein include a system having memory configured to store computer executable instructions and data; a network interface configured to enable communication of data with at least one networked device; and a processor for executing the computer executable instructions, wherein the system is configured to at least store manufacturing logic for enabling the modification of optical manufacturing data.

In various embodiments, the above system may be an at least one of a system is a LDS, a LMS, a Rx lab network device (e.g., a server), and/or a Rx lab equipment. In various embodiments, the above system may either be configured to communicate the manufacturing logic to one or more systems and/or use the manufacturing logic to modify the optical manufacturing data for an optical job to generate modified optical manufacturing data. The modified optical manufacturing data is then used in the manufacturing process of the optical job.

Other aspects and advantages of the invention will be apparent from the following description and the appended claims.

BRIEF DESCRIPTION OF THE DRAWINGS

Illustrative embodiments of the present invention are described in detail below with reference to the attached drawing figures, which are incorporated by reference herein, and wherein.

Figure 1:
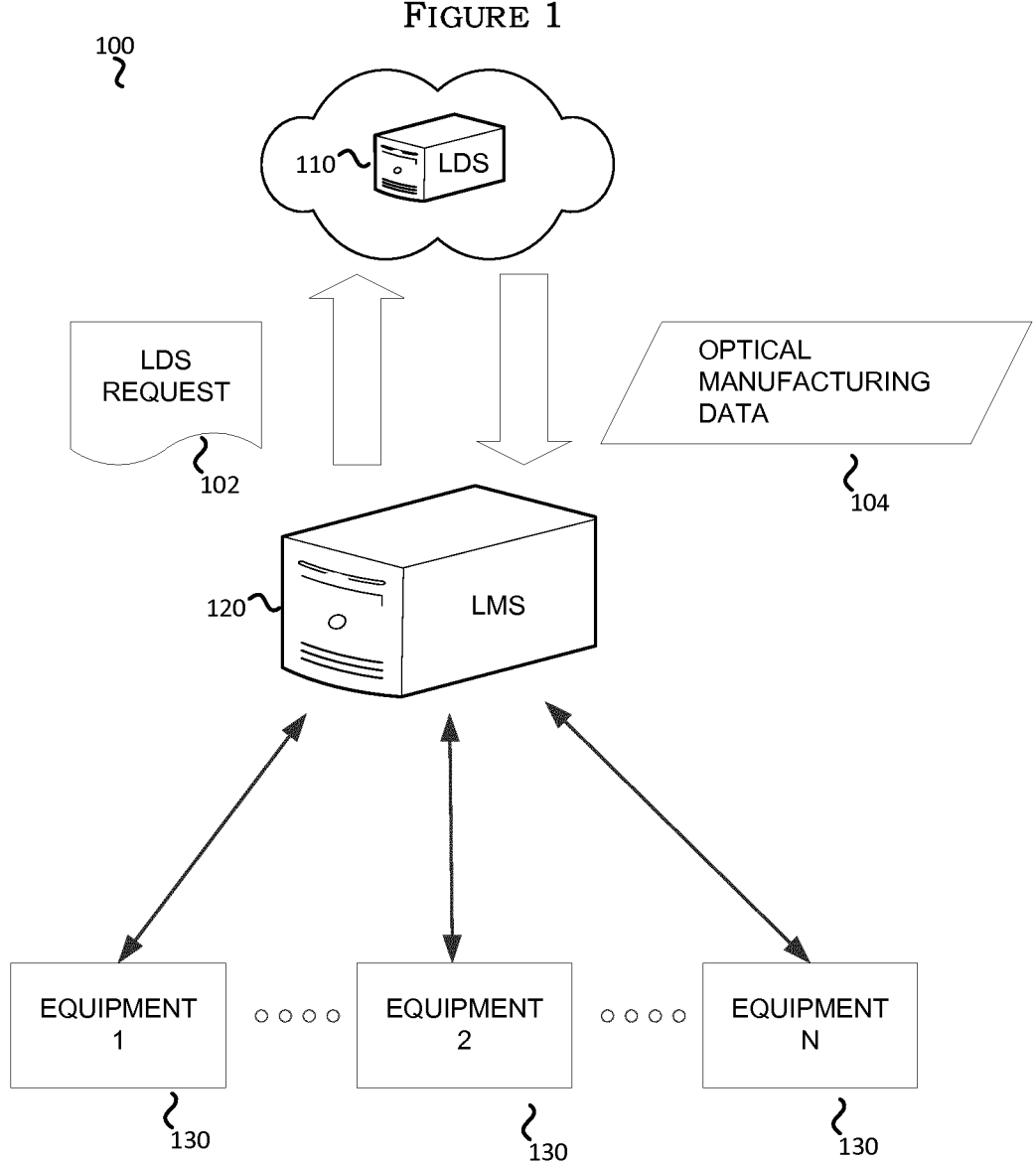
FIG. 1 illustrates a prior art system configuration that is currently being used in the manufacturing process of optical lenses.

The illustrated figures are only exemplary and are not intended to assert or imply any limitation with regard to the environment, architecture, design, or process in which different embodiments may be implemented.

DETAILED DESCRIPTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments is defined only by the appended claims.

Additionally, as used within the written disclosure and in the claims, the terms "including" and "comprising" are used in an open-ended fashion, and thus should be interpreted to mean "including, but not limited to". Unless otherwise indicated, as used throughout this document, "or" does not require mutual exclusivity. In addition, as used herein, the singular forms "a", "an" and "the" are intended to include the plural forms as well, unless the context clearly indicates otherwise.

The terms "system", "device", and "machine" is intended to mean one or more specially configured apparatus with each apparatus having the necessary hardware and software configuration for performing the claimed functions. For example, at a minimum, each apparatus would include at least one processing unit or processor for executing instructions, memory for storing the instructions and other data used by the processor, and one or more communication interfaces such as input/output interfaces for receiving and displaying information and network interfaces for communicating data over a network. The instructions may include, but are not limited to, machine code instructions, bytecode for a software interpreter, object code, and source code in a high-level programming language. The apparatus may also include input devices such as, but not limited to, a keyboard, a mouse, and a touchscreen. In some embodiments, the apparatus may be configured to receive audio or visual input. The apparatus may also include one or more output devices such as a monitor, projection screen, or a built-in display. Non-limiting types of apparatus include, but are not limited to, stand-alone computers, networked computers, servers, mobile computing devices, and smartphones, tablets, or similar devices.

Unless specified, the network interfaces may include both wired and wireless communications that support any type of communication protocol for exchanging data over any type of public or private network. Unless specifically claimed, the term network includes, but is not limited to, the Internet, a mobile cellular or data network, an intranet, a personal area network, local area network, metropolitan area network, enterprise private network, storage area network, and virtual private network.

In addition, unless otherwise specified, any use of any form of the terms "connect," "engage," "couple," "attach," "communicate," or any other term describing an interaction between elements is not meant to limit the interaction to direct interaction between the elements and may also include indirect interaction between the elements described.

As used herein, the term "logic" means executable instructions such as, but not limited to, pre-compiled, compiled or semi-compiled executable code such as scripts, algorithms, functions, and classes that are written in any programming language. The term "manufacturing logic" means logic that enables the modification of optical manufacturing data generated by a LDS in response to a LDS request as described herein. The term "optical manufacturing data" means data, calculations, and/or measurements that indicate a lens design criteria based on information associated with an optical job contained in a LDS request as described herein.

Further, certain embodiments of the invention may be stored in a tangible computer-readable program product, such as, but not limited to, a hard disk drive, random access memory, read only memory, electrically erasable programmable read-only memory, flash memory or other memory technology, compact disc, digital versatile disks or other optical disk storage, magnetic cassettes, magnetic tape, magnetic disk storage or other magnetic storage devices.

Referring now to the drawings, FIG. 1 illustrates a prior art system 100 configuration that is currently being used in the manufacturing process of optical lenses. The prior art system 100 includes a lens design system (LDS) 110, a lab management system (LMS) 120, and a plurality of laboratory equipment 130.

The LMS 120 is typically located at an optical lens manufacturing facility also referred to herein as an Rx lab. The LMS 120 executes lab management software for controlling the manufacturing of optical lens that are being processed on the plurality of laboratory equipment 130 at the Rx lab, referred to herein as optical jobs or jobs. The process typically starts with a blank, made of glass or organic material that is cut or grinded and polished into its desired form.

The plurality of laboratory equipment 130 may include a generation tool that generates the basic shape of the lens into the blank such as creating the convex or concave surface of the lens, a blocker that is used to mechanically position and hold in position the semi-finish during the surfacing process, a polisher for polishing the lens and fine tuning the curvature and thickness of the lens, a bevel and centering tool for centering the optical axis co-linear with the mechanical axis, an edger equipment for the generation of the shape of the lens during the finishing process, and a laser for engraving, and a vacuum or coating chamber for applying a coating material to the lens.

The LDS 110 is configured to design a lens to meet a set of performance requirements and constraints. These requirements and constraints are submitted to the LDS 110 by the LMS 120 in an LDS request 102 typically either through a web service or through a local server installation. The LDS request 102 may include parameters such as, but not limited to, a patient's prescription; a job number, a lab number, frame information, design to calculate such as surface profile types (spherical, aspheric, holographic, diffractive, etc.); radius of curvature; distance to the next surface; material type; optionally tilt and decenter values; edge thicknesses; minimum and maximum air-spaces between lenses; maximum constraints on entrance and exit angles; physically realizable mass index of refraction and dispersion properties; optical performance quality; physical requirements such as weight, static volume, dynamic volume, center of gravity and overall configuration requirements; environmental requirements such as ranges for temperature, pressure, vibration and electromagnetic shielding; and manufacturing cost.

Once the LDS 110 determines the lens design criteria based on the LDS request received from the LMS 120, the LDS 110 sends the optical manufacturing data 104 back to the LMS 120. For instance, non-limiting examples of information contained in the optical manufacturing data 104 may include the product definition of an optical job to manufacture (e.g., design, material, index), optical definition of the lens to manufacture, geometrical definition of lens to manufacture, surface matrix, and manufacturing parameters. The LMS 120 then uses the information contained in the optical manufacturing data 104 to control the processing of the optical job on the plurality of laboratory equipment 130. For example, in one embodiment, once the optical manufacturing data 104 is received, information contained in the optical manufacturing data 104 is dispatched to the appropriate equipment when the job is scanned during the manufacturing process.

Currently, in order for this process to work, the LDS 110 requires knowledge of every parameter and configuration of each of the equipment in the Rx lab involved in the manufacturing process. If the LDS 110 is not aware of every piece of equipment involved in the processing of an optical job, or a configuration of one equipment involved in the processing of an optical job, then the production of the lens in the Rx lab may be incorrect. For example, errors associated with surface orientation, incorrect compensations, incorrect engraving location or inconsistent optics may occur.

Additionally, all of the exchanges between the LDS 110 and LMS 120 are strictly static data exchanges. For example, the prior art system 100 takes static data (the LDS request 102) as input and returns static data (the optical manufacturing data 104) as output. This static data prevents the receiver of the data (i.e., the LMS 120 and the plurality of laboratory equipment 130) from adapting the data to the specific equipment configuration as it is almost impossible for the LMS 120 or the plurality of laboratory equipment 130 to rework the data sent by the LDS 110.

Thus, based on the current design, when a design vendor wishes to deploy a new design to be manufactured in an Rx lab, the following, among others, must be accomplished: 1) the new product must be entered in the LMS 120; 2) the new engraving logos must be added inside the laser; 3) the LDS 110 must know the orientation of the surface matrix to send to the generator; 4) the LDS 110 must know what blocking axis is used in the lab (physical orientation of the lens on the block); 5) the LDS 110 must know what tooling and consumables are available such as, but not limited to, blocking ring, polishing pads, and the radius of generator fine cutting tool; and 6) the LDS 110 must know how the laser and generator chucks are positioned and how the equipment are configured in order to know what the orientation (and position) of the surface and the engravings will be after these steps of the process.

Additionally, if a design vendor or an equipment manufacturer wishes to deploy a new process or new technology to the lab, the following actions including, but not limited to, must be accomplished: 1) integration of the equipment within the production line; 2) connection of the equipment with the LMS 120 including knowledge of what data the equipment must receive from the LMS 120 and what data the equipment will send to the LMS 120; 3) integration of the equipment within the software chain (LMS 120 and LDS 110) in order to get the right data calculated in the way the equipment software expects it or in order to get the proper equipment output.

In both design and process/technology deployment situations to Rx labs, all parties (LDS, LMS, equipment vendors) must collaborate to achieve the result because the LDS 110 and the LMS 120 software must know how to calculate and deliver the static data to the equipment in such a way that the achieved results match the expectations. Thus, it can be seen that the current configuration and process of the prior art system 100 is not easily adaptable to changes.

Figure 2:
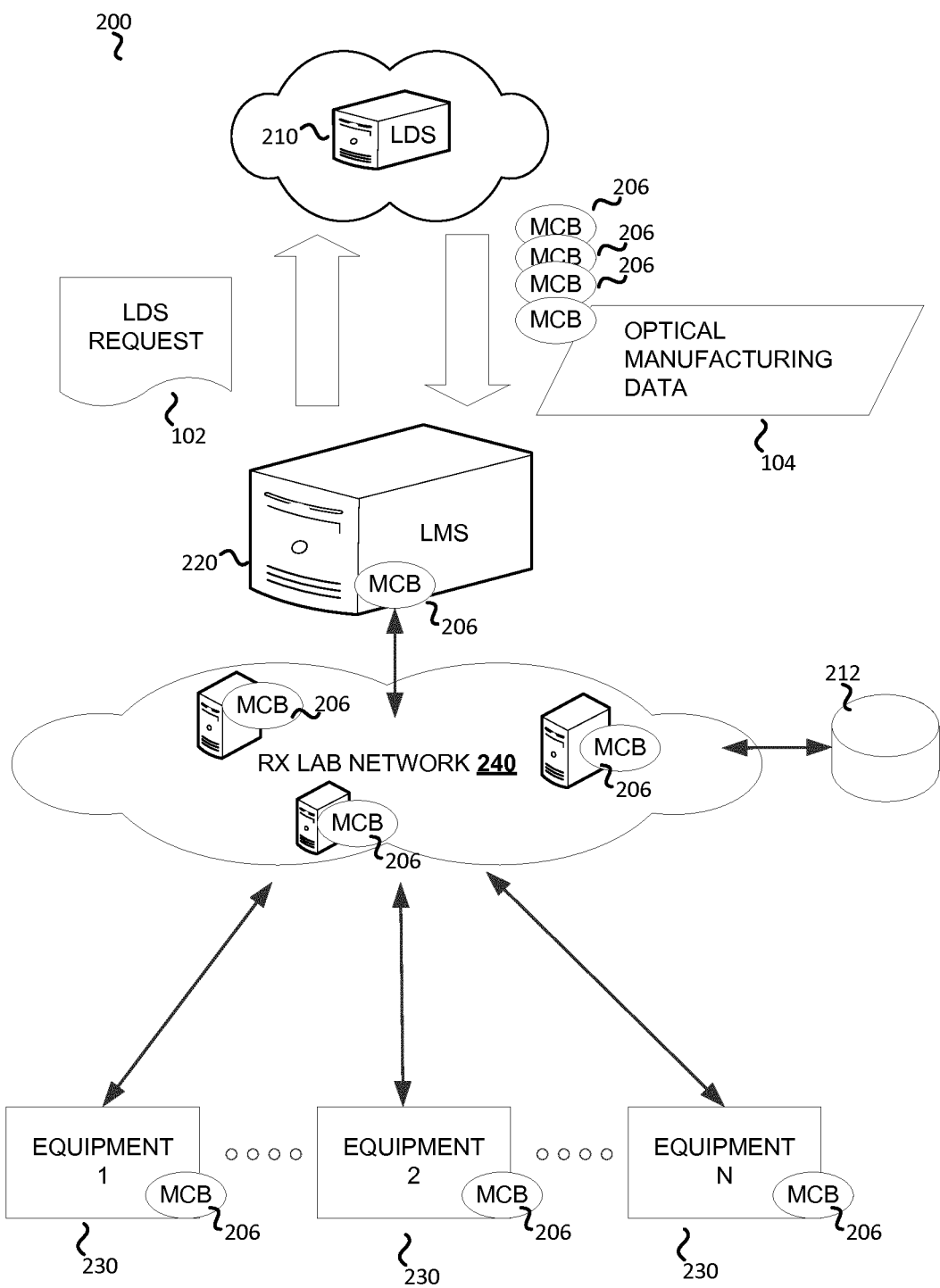
FIG. 2 illustrates a system for use in the manufacturing process of optical lenses in accordance with a disclosed embodiment.

Accordingly, the disclosed embodiments seek to provide one or more improvements on the prior art system 100. One such embodiment is shown in FIG. 2, which depicts a system 200 for use in the manufacturing process of optical lenses. In the depicted embodiment, the system 200 includes a LDS 210, a LMS 220, and a plurality of laboratory equipment 230. The LDS 210, LMS 220, and the plurality of laboratory equipment 230 performs all the functions associated with the corresponding devices described in the prior art system 100. However, in accordance with the disclosed embodiments, the LDS 210 is configured to not only communicate the static optical manufacturing data 104, but also enable the exchange or the sharing of logic. For instance, in one embodiment, the LDS 210 is configured to provide logic bricks, referred to as manufacturing computation blocks (MCBs) 206 in FIG. 2, that the receiver (the LMS 220 and/or the plurality of laboratory equipment 230) may use to rework the static data.

In some embodiments, in addition to the LDS 210 providing MCBs 206, the MCBs 206 could also be developed, shared, or provided by an equipment manufacturer or an LMS software provider. For instance, in one embodiment, the MCBs 206 may be stored on a Rx lab network 240 comprising of one or more networked devices. The MCBs 206 may also be stored on the LMS 220 or on any of the plurality of laboratory equipment 230.

In addition, the MCBs 206 may take the form of executable computer code that may be executed by any of the systems in the Rx lab (e.g. the LMS 220, any of the systems within the Rx lab network 240, and/or by any of the plurality of laboratory equipment 230). For example, in one embodiment, each MCB is an independent piece of code that may be executed to rework the static data returned by the LDS 210 or calculated by the LMS 220 or any equipment 130. For instance, in one embodiment, every system involved in the Rx lab generates some form of data. For example, the LDS 210 may generate optics related data as well as certain manufacturing parameters for the plurality of laboratory equipment 230, the LMS 220 may also calculate certain manufacturing parameters, and each of the plurality of laboratory equipment 230 may calculate measurements, or provide information regarding their settings or their status (e.g. number of cuts generated with the currently installed tool in the generator).

In one embodiment, all this data may be stored and shared as a data pool 212 accessible by the MCBs 206 or the system executing the MCBs. The data pool 212 may be stored using one or more databases, or by any other method of storing and organizing data. In one embodiment, as each member of the system 200 generates new data or updates existing data, the new data may be shared with the other MCBs 206 and/or systems through the update of the common static data pool 212. For example, in one embodiment, the LMS 220 may be configured to associate certain data types (or OMA tags) to certain MCBs such that the MCBs are notified as soon as the data types are updated. Non-limiting examples of the types of OMA tags include, but not limited to, KPRVM/KPRVA tags associated to blocker, AVAL/SVAL tags associated to generator and laser, and BLKD tag associated to blocker and generator.

Thus, one advantage of the disclosed embodiments is that it would ease the deployment of manufacturing calculation systems such as the LDS 110 as described above with respect to FIG. 1, which depicts a centralized system that requires knowledge of the entire Rx lab floor (equipment, process, configurations . . . ). For instance, using the distributed system disclosed herein, the output of one system (e.g., the LDS 210) is decoupled from the input of the other systems by the means of distributed logic bricks that may be executed after the static data is generated by one system and before it is consumed by the other systems. The term "distributed" as used herein means not centralized. For instance, the distributed system disclosed herein prevents any-one system such as the LDS 210 from having to centralize all the information regarding each piece of equipment and every configuration of each of the equipment before calculating all the required data. Instead, if an Rx lab uses a manufacturing equipment or process that is unknown to the LDS 210, the new equipment or process could be easily integrated if the equipment manufacturer itself provides a MCB/logic block to the Rx lab network 240. Thus, the LDS 210 provider and the equipment manufacturer would not have to collaborate and start significant developments in order to integrate the new equipment or process within the LDS 210. Accordingly, the disclosed embodiments would ease the deployment of new technologies, new processes and new products to Rx labs. In addition, the deployment time for new technologies, processes and new products would be greatly reduced.

As described in the previous paragraphs, the disclosed embodiments enable more than just static data exchanges between the various devices involved in the manufacturing process of optical lenses. For instance, instead of exchanging simple text files with data formatted with tags (c.f. Vision Council Digital Communication Standard), the exchanges would consist of packets of logic plus data. As described above, in one embodiment, the packets of logic (MCBs) and the optical manufacturing data are maintained and communicated separately. However, in an alternative embodiment, the packets of logic (MCBs) and the optical manufacturing data are combined into a single data/logic block referred to herein as a Job Computation Block (JCB). Each JCB would be associated with a particular optical job. Additionally, each JCB may be communicated over a network in one or more data packets.

Figure 3:
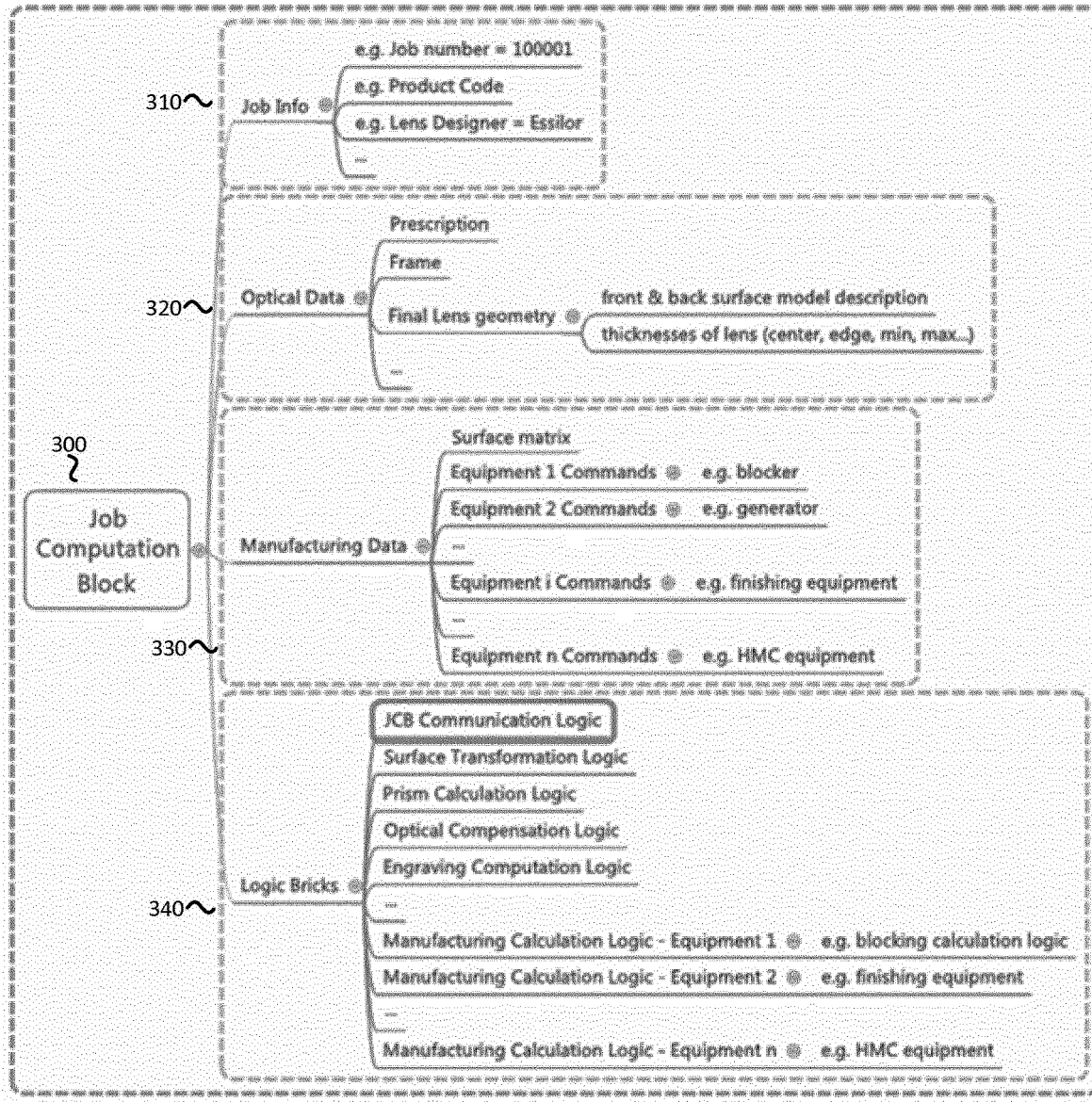
FIG. 3 illustrates a Job Computation Block (JCB) in accordance with a disclosed embodiment.

As an example, FIG. 3 illustrates a Job Computation Block (JCB) 300 in accordance with one embodiment. In the depicted embodiment, the JCB 300 comprises job information 310, optical data 320, manufacturing data 330, and logic bricks 340.

Non-limiting examples of data contained in the job information 310 may include an optical job number, a product code, and a lens designer. The optical job number corresponds to an optical job that the JCB 300 is associated with. The product code indicates the reference of the product being manufactured including a description of the design and material for the product. The lens designer indicates the party/manufacturer that generated the design parameters for the lens.

Non-limiting examples of data contained in the optical data 320 may include a patient's prescription, frame information such as model and sizing information, and final lens geometry such as from and back surface model description, and thicknesses of lens (center, edge, min, max . . . ).

Non-limiting examples of data contained in the manufacturing data 330 may include a surface matrix and commands for a plurality of equipment in the Rx lab such as, but not limited to, a blocker, generator, finishing equipment, and coating equipment. The surface matrix data describes the surface to be grinded by the generator (front or back). Non-limiting examples of commands that may be provided to the plurality of equipment include a macro code to send to the polisher (defines the cycle time, speed, movement of the polishing pad . . . ), a macro code to send to the generator (the macro defines the speed of rotation, the tools to use . . . ), and/or a thickness command for the generator (initial and final thickness of the lens block geometry).

The logic bricks 340 contain a plurality of functions/logic code. Non-limiting examples of logic contained in the logic bricks 340 may include JCB communication logic, surface transformation logic, prism calculation logic, optical compensation logic, and engraving computation logic.

The JCB communication logic may include logic for, but not limited to, disposing of the JCB object after a job is completed, responding to a broadcast to let other parties/systems know that the job is still active, and/or provide the state of the calculation/manufacturing status.

The surface transformation logic may include logic for, but not limited to, enabling the manipulation of the surface matrix such as, but not limited to, adding prism, adding spherical compensation, and/or modifying its orientation or position (horizontal or vertical movement).

The prism calculation logic may include logic for, but not limited to, adding or removing prism, or calculating the distribution of prism across the various equipment in case of a change in manufacturing line.

The optical compensation logic may include logic for, but not limited to, calculating the addition or subtraction of optical power layers to add to the surface matrix. The engraving computation logic may include logic for, but not limited to, enabling the re-calculation of the position or orientation of the engravings.

In addition, the logic bricks 340 may include manufacturing calculation logic for one or more equipment. The manufacturing calculation logic are configured to adapt the commands sent to the equipment. Non-limiting examples of logic contained in the manufacturing calculation logic may include, but not limited to, surfacing calculation logic, finishing equipment calculation logic, and coating equipment calculation logic.

The surfacing calculation logic may include logic for, but not limited to, calculating: 1) the specific data for the blocker equipment—blocking ring to use, prism to block, position of the semi-finish during blocking step; 2) the specific data for the generator equipment: macros, thicknesses, etc.; and 3) the specific data for the polisher equipment: polishing tool, polishing macro, etc.

The finishing equipment calculation logic may include logic for, but not limited to, calculating: 1) the macros for the laser equipment, the position of the engravings; 2) the macros for the edging equipment: macros, tools to use; and 3) the coating equipment calculation logic may include logic for, but not limited to, enabling.

The coating equipment calculation logic may include logic for, but not limited to, calculating: 1) what consumables/coatings to use; and 2) what process parameters to use.

The logic bricks included in this JCB 300 may be implemented in various ways including, but not limited to, (1) simple scripting language written as text that is then read and interpreted by the receiver of the JCB, (2) compiled executable code that is executed by the receiver, (3) compiled or semi-compiled executable code that is executed within a virtual machine either by the receiver of the JCB or on a network of servers hosting the virtual machine. In certain embodiments, the implementation selected will depend on the level of confidentiality and IS security required. Additionally, in some embodiments, the script may be encrypted to enhance security.

Figure 4:
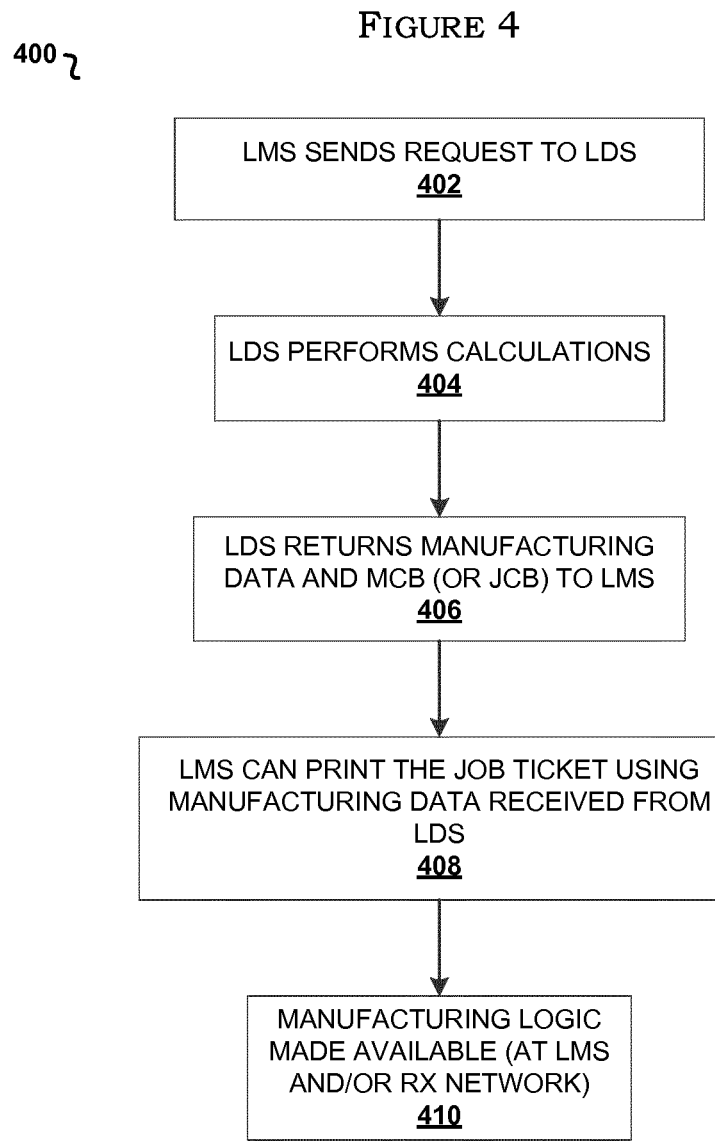
FIG. 4 illustrates a flow chart depicting a process for distributing optical manufacturing data and manufacturing logic in accordance with a disclosed embodiment.

FIG. 4 illustrates a flow chart depicting a process 400 for distributing optical job and manufacturing computation data in accordance with one embodiment. As done today, the process 400 begins at step 402 with the LMS sending a request (i.e., an LDS request) to the LDS in order to manufacture the job. Depending on the implementation, the LDS request may be sent either through a web service or through a local server installation. At step 404, the LDS performs the calculations based on the information contained in the LDS request to determine optical manufacturing data for an optical job. The LDS, at step 406, returns the optical manufacturing data and MCB, or alternatively a JCB, to the LMS after calculation of the job.

Once received, the LMS, at step 408, may be configured to print a job ticket using the original data received within the JCB. At step 410, the JCB is made available to the equipment by the LMS. In one embodiment, the JCB is made available to the equipment in the lab by either hosting the execution of the JCB within the LMS or deploying it to network of servers where the logic can be executed. Whether the logic is executed at the LMS level (by the LMS, or within a virtual machine) or on the Rx lab's network (by a set of servers), the equipment can manufacture the job by broadcasting requests on the Rx lab network or to the LMS in order to receive the proper commands. In one embodiment, a communication channel may be established between the equipment and the JCB using a TCP/IP type protocol.

Figure 5:
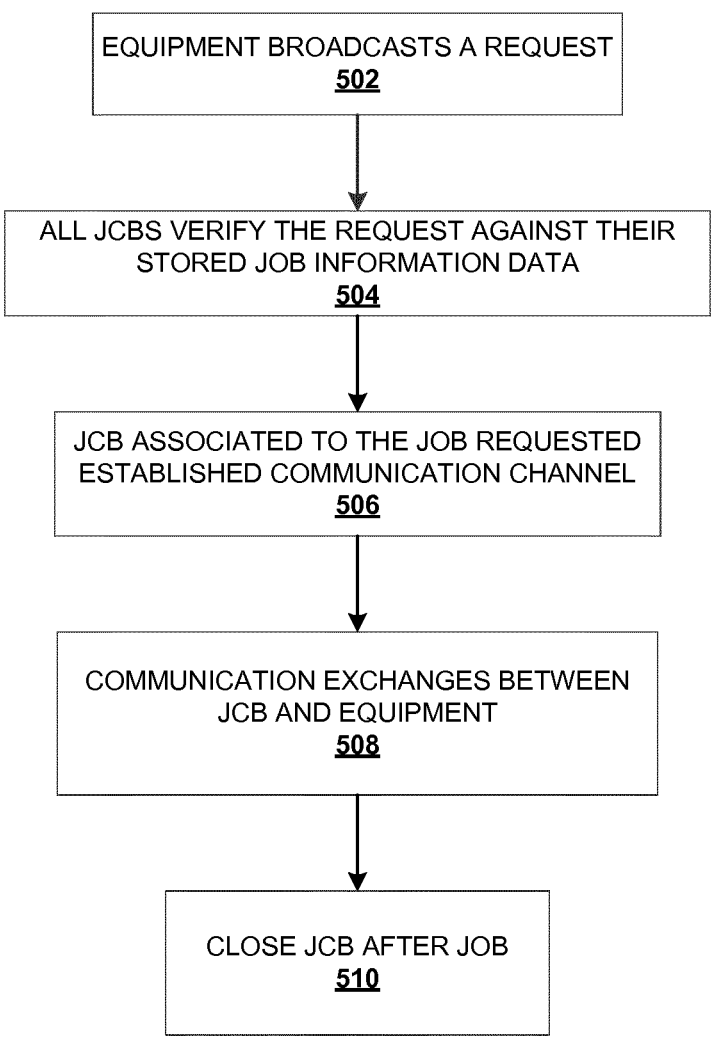
FIG. 5 illustrates a flow chart for establishing a communication channel between a Rx lab equipment and the JCB in accordance with an embodiment.

For example, FIG. 5 illustrates a flow chart for establishing a communication channel between the equipment and the JCB in accordance with an embodiment. Beginning with step 502, the equipment will broadcast a request calling for the JCB associated to the job scanned at the equipment. Once the request is broadcasted, at step 504, all JCBs verify the request against the job information data they store (e.g., using the JCB communication logic). At step 506, the JCB associated to the job requested then responds to the equipment dictating the communication channel to use (e.g. TCP port, JCB reference number . . . ). The communication is now established and communication exchanges may occur at step 508.

Figure 6:
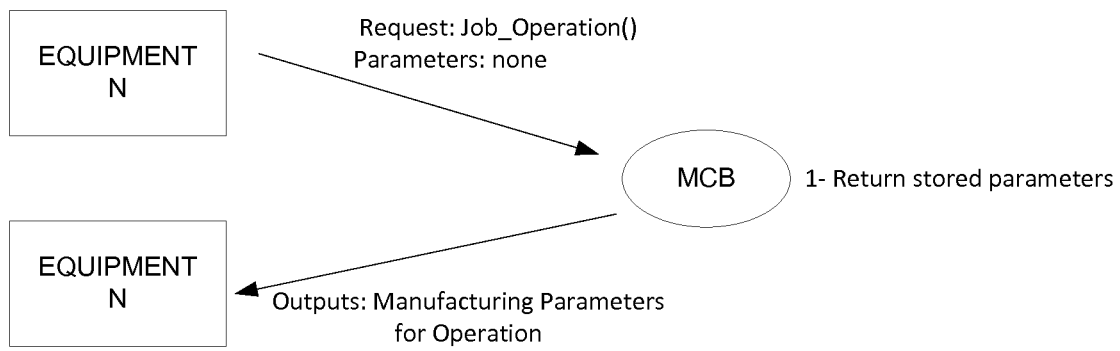
FIG. 6 illustrates an equipment operation request between a Rx lab equipment and the JCB in accordance with an embodiment.

In one embodiment, once the communication is established, the equipment may proceed in one of two ways. One way is illustrated in FIG. 6 in which the equipment sends a DCS request with a list of data required (e.g., a list of OMA tags) to the JCB. For instance, the equipment may send a DCS request with the function Job Operational( ) containing no function parameters to the JCB. The JCB executes the function Job Operational( ) with no function parameters to retrieve the stored parameters. The JCB then returns the manufacturing parameters for operation back to the equipment.

Figure 7:
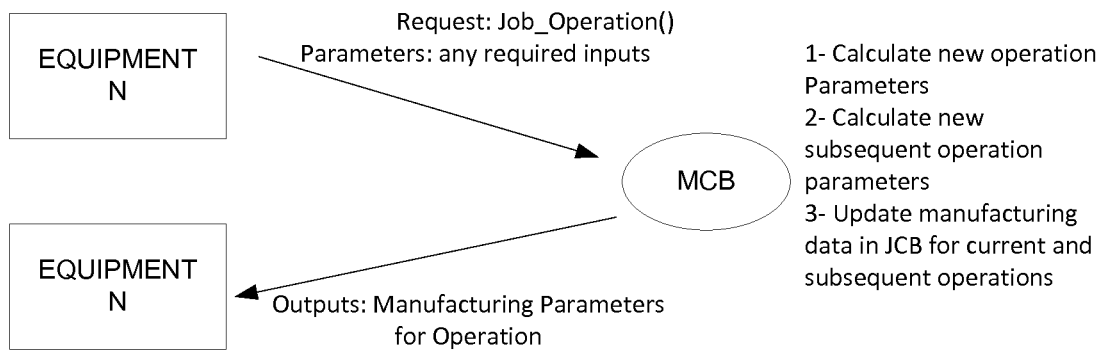
FIG. 7 illustrates an equipment operation update request between a Rx lab equipment and the JCB in accordance with an embodiment.

Alternatively, in another embodiment, in order to leverage the new JCB system, the equipment may send a request that triggers the appropriate logic bricks. For example, as illustrated in FIG. 7, the equipment sends a DCS request with the function Job Operational( ) along with any relevant parameter inputs such as, but not limited to, inputs for required change request, outputs from equipment operation, and measurements. In this embodiment, the JCB will run the logic code required to adjust the original data and send the corrected data to the equipment. It will also re-calculate any manufacturing data impacted by this change (for any subsequent operation). The JCB then returns the updated manufacturing parameters for operation back to the equipment.

Referring back to FIG. 5, after the job is successfully processed, at step 510, the JCB object may be closed/deleted from the network. This may be achieved by the LMS or by the last equipment to process the job. For example, in one embodiment, the caller may establish a connection with the JCB as described above and send it a Job Completed( ) request that will automatically trigger the closing of the JCB object.

Figure 8:
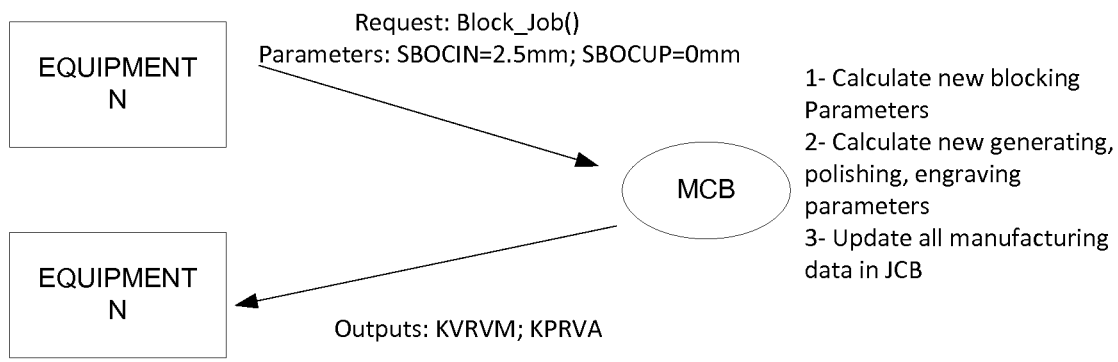
FIG. 8 illustrates an example of a blocker equipment communicating with a JCB in accordance with an embodiment.

Referring now to FIG. 8, an example of a blocker equipment communicating with a JCB in accordance with an embodiment is presented. In this example, the blocker equipment (surfacing process) is used to block the lens. When a job is scanned at the blocker equipment, the blocker follows the broadcast process described above to establish communication with the JCB for that current job.

Once the communication is established, the blocker equipment sends a request for receiving blocking data in order to block the job at a different semi-finishing blocking location than originally calculated by the LDS. In one embodiment, this triggers a blocking calculation logic brick within the JCB. The blocking calculation algorithm will re-calculate the job's manufacturing data in order to position the lens on the block as instructed by the equipment.

If the blocker wishes to change the blocking orientation, it may also include that in the request and the JCB's logic would then re-calculate the surface matrix to send to the generator. Additionally, in some embodiments, the JCB's logic could also calculate new generating, polishing, and engraving parameters. The JCB would then update all the manufacturing data in the JCB. The JCB would then return the new blocking parameters to the blocking equipment such as KPRVM and KPRVA as defined by the data communication standard set by the Vision Council. As known by a person of ordinary skill in the art, the Vision Council represents manufacturers and suppliers of the optical industry and sets communication standards that are shared by manufacturers of optical laboratory equipment and producers of software used in optical laboratories. For example, KPRVM indicates the magnitude of blocked prism and KPRVA is the base setting at which to block KPRVM, 0-360 degrees.

Figure 9:
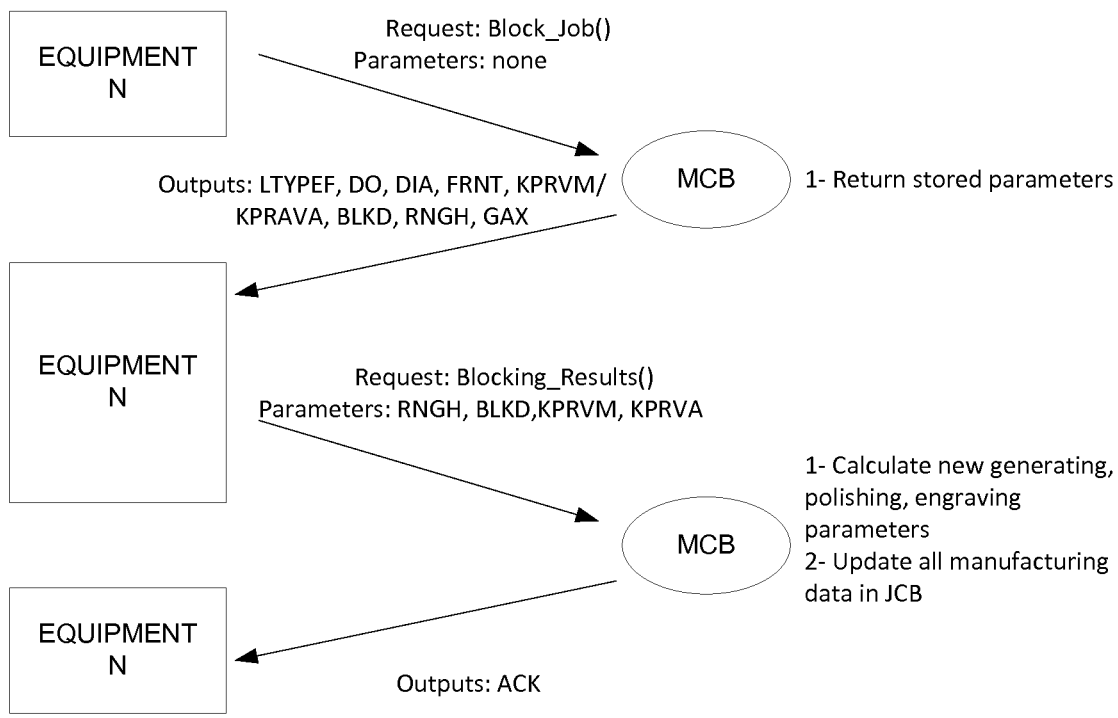
FIG. 9 illustrates an example of automatic blocker equipment communicating with a JCB in accordance with an embodiment.

FIG. 9 illustrates an example of an automatic blocker equipment communicating with a JCB in accordance with an embodiment. In this embodiment, the automatic blocker equipment may call the JCB to simply retrieve the original data. In this case, the JCB retrieves and returns the stored parameters such as, but not limited to, LTYPEF (indicating lens type), DO (indicating right eye, left eye or both), DIA (indicating blank diameter), KPRVM, KPRVA (indicating prism to be blocked), BLKD (indicating diameter of the block), RNGH (indicating ring height), and GAX (indicating cylinder axis).

Alternatively, if the blocker selects a different blocking configuration (e.g., different blocking ring, insert, position, orientation), the automatic blocker equipment may then send to the JCB the actual blocking parameters (e.g., Blocking_Results(RNGH, BLKD, KPRVM, KPRVA)). In this case, the JCB's logic will calculate new parameters such as, but not limited to, generating, polishing, and engraving parameters and adjust the remainder of the manufacturing parameters to account for this change (e.g., update block dimensions—AVAL, SVAL, cribbing diameters if necessary . . . ). Either the JCB or the automatic blocker equipment can be configured to send this updated data to the processing equipment such as generator or polisher. In one embodiment, the JCB will return an acknowledgment to the automatic blocker equipment acknowledging completion of the request.

In addition to being able to modify equipment operation, the disclosed embodiments may also be utilized if there is a manufacturing line change. For example, if the job is calculated for one given DS manufacturing line, but the LMS may decide that it wants to route the job to a different DS manufacturing line. Reasons for this occurring include, but not limited to, the job exceeds the process capabilities/parameters of the line used by the LDS, lab flow optimization, job routing, and product routing.

In today's Rx labs, once the LDS data is calculated for a given Rx process (e.g. alloy DS process or alloy-free DS process), the LMS isn't capable of fully recalculating manufacturing data for a different process than calculated by the LDS. However, using the disclosed embodiments, the JCB for that given job may be called and requested to re-compute the manufacturing data for a different manufacturing process. For example, in one embodiment, the JCB may re-compute the manufacturing data for a new line that has different process capabilities (max prism, max diameters, max curves . . . ), for a new line that doesn't behave the same way and doesn't require the same type of compensations (e.g. polishing add compensations), and/or for a new line that doesn't use the same type of process (e.g. alloy VS alloy-free).

In one embodiment, the LMS (or the first equipment that the job is scanned at: e.g., a blocker equipment) is configured to request to the JCB of that job to re-compute all manufacturing parameters (e.g. send request Calculate_AlloyFree( ) function). The subsequent equipment may then simply request the updated stored manufacturing parameters.

Additionally, the disclosed embodiments may be used to calculate updated generating and engraving parameters for the subsequent operations based on an actual measurement of the lens's position on a surfacing block. For instance, some equipment are used in Rx labs to measure or obtain certain properties of the lens being manufactured in order to adapt following manufacturing steps in order to properly manufacture the lens or obtain a manufactured lens closest to the Rx as possible.

Figure 10:
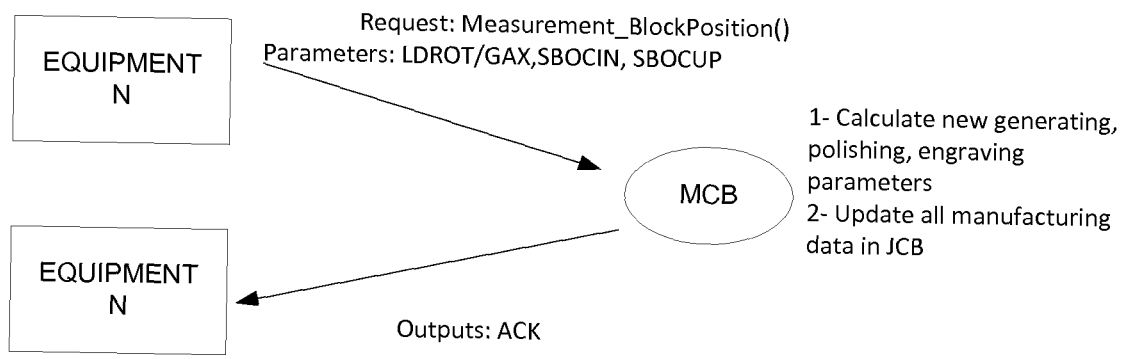
FIG. 10 illustrates an example of a measurement equipment communicating with a JCB in accordance with an embodiment.

One example of this is the measurement of the position of the lens on the surfacing block as illustrated in FIG. 10. In this case, this measurement may be used to adjust the commands sent to the generator in order to properly place and orientate the optics of the convex side of the lens relative to the concave side of the lens. This is done in order to achieve the best possible design. In addition, this measurement may be used to adjust the commands sent to the laser in order to properly place and orientate the engravings on the lens.

In this embodiment, the equipment providing the measurement of the lens's position on the surfacing block may communicate to the JCB the actual position of the lens on the block which would trigger the calculation of updated generating and engraving parameters for the subsequent operations.

In another embodiment, the MCBs may be autonomous and not tied to a particular job. For example, in one embodiment, autonomous MCBs may reside on the Rx lab network as shown in FIG. 2. In one embodiment, the autonomous MCBs may be configured to send update requests to the LDS to see if any new algorithm or update is released. In one embodiment, each autonomous MCB is triggered autonomously in response to a call for a given piece of data corresponding to an autonomous MCB.

The disclosed embodiments could also be used for optical product calculation (e.g., Vx S SF selection, range data, SF logistic/geometry data . . . ). In such a system, the LDS could be configured to compute the main optical design features, but distributed logic could be leveraged by the LMS to automatically accomplish, among other things, Rx range, select SF for job (geometry of SF, logistic data—OPC), and optical compensations.

In conclusion, advantages of the disclosed embodiments over the current art include, but are not limited to, the capability to adjust a job manufacturing (or optical) data using the JCB logic, compensate a job in real time with measuring equipment calling JCBs, re-compute a job to change manufacturing line, add an equipment and (in combination or separately from) a LDS design without impact to LMS, and adapt manufacturing parameters without calling back LDS. In addition, the LDS doesn't have to know equipment present and their configuration as the logic is in the JCB to be adapted to equipment at the last moment The disclosed embodiments could be used by Rx labs, LMS (Lab Management Software) software providers, LDS (Lens Design System) providers, and equipment manufacturers. All these systems could benefit from using the previously described common logic exchange system in order to simplify the deployment of calculation systems, processes and new technologies to Rx labs. For example, the design vendors would benefit from reduced TTM (Time To Market). Equipment manufacturers would benefit from increased interoperability of their equipment with LDS and LMS software. LMS developers would benefit from reduced constraints from the LDS and more autonomy on configuring the lab with its owner.

The above disclosed embodiments have been presented for purposes of illustration and to enable one of ordinary skill in the art to practice the disclosed embodiments, but is not intended to be exhaustive or limited to the forms disclosed. Many insubstantial modifications and variations will be apparent to those of ordinary skill in the art without departing from the scope and spirit of the disclosure. For example, the steps and components described in the disclosed embodiments are merely illustrative and do not imply that any particular step or component is a requirement of a disclosed embodiment or that a particular process or step must be performed in a particular order. For instance, although the flowcharts depict a serial process, some of the steps/blocks may be performed in parallel or out of sequence, or combined into a single step/block. The scope of the claims is intended to broadly cover the disclosed embodiments and any such modification.

Additionally, although specific terms are employed herein, they are used in a generic and descriptive sense only and not for purposes of limitation. For instance, the term database, as used herein, is intended to include any form of organized data, including, but not limited to, data found in tables, charts, spreadsheets, and documents. Furthermore, the term database does not imply the use of any particular or specialized database software nor does it imply the use of any particular data structure.

As non-limiting examples, variations of different embodiments disclosed herein include, but are not limited to, the following:

Clause 1. A distributed optical job and manufacturing computation system comprising: a lens design system configured to receive an optical lens design request for an optical job; a lab management system in communication with the lens design system, the lab management system configured to send the optical lens design request to the lens design system, wherein the lens design system is configured to determine optical manufacturing data in response to the optical lens design request, and wherein the lens design system is configured to communicate the optical manufacturing data and manufacturing logic to the lab management system; and a plurality of optical manufacturing equipment in communication with the lab management system, wherein the lab management system is configured to manage the workflow of optical jobs using the plurality of optical manufacturing equipment.

Clause 2. The distributed optical job and manufacturing computation system of Clause 1, further comprising a lab network that includes at least one server, wherein the lab network is configured to communicate with the lab management system and the plurality of optical manufacturing equipment.

Clause 3. The distributed optical job and manufacturing computation system of Clauses 1 or 2, wherein the manufacturing logic is stored and executed at the lab management system.

Clause 4. The distributed optical job and manufacturing computation system of Clause 2, wherein the manufacturing logic is stored and executed on the lab network.

Clause 5. The distributed optical job and manufacturing computation system according to any of Clauses 1 or 2, wherein the manufacturing logic is stored and executed by at least one of the plurality of optical manufacturing equipment.

Clause 6. The distributed optical job and manufacturing computation system according to any of Clauses 1-5, wherein the optical manufacturing data and manufacturing logic are grouped together as a job computation block.

Clause 7. The distributed optical job and manufacturing computation system according to any of Clauses 1-6, wherein the job computation block is deleted following a completion of the optical job.

Clause 8. The distributed optical job and manufacturing computation system according to any of Clauses 1-7, wherein the manufacturing logic comprises logic for an optical lens blocker to recalculate blocking parameters for the optical job based on conditions of the optical lens blocker.

Clause 9. The distributed optical job and manufacturing computation system of Clauses 1 or 2, wherein the manufacturing logic comprises logic that enables 1) the modification of optical manufacturing data for a particular equipment along a process line associated with the optical job, and/or 2) the modification of optical manufacturing data for subsequent equipment along the process line associated with the optical job.

Clause 10. The distributed optical job and manufacturing computation system of Clause 10, wherein the manufacturing logic comprises logic for: 1) an optical lens blocker to recalculate blocking parameters for the optical job based on conditions of the optical lens blocker, 2) re-computing the optical manufacturing data for a different manufacturing process, and/or 3) calculating updated generating and engraving parameters (and optionally, polishing, and edging parameters) based on a measurement carried out during the manufacturing process, such as, but not limited to, a position of a lens on a surfacing block.

Clause 11. The distributed optical job and manufacturing computation system according to any of Clauses 1-10, wherein the manufacturing logic is provided by or shared by an equipment manufacturer or an LMS software provider.

Clause 12. The distributed optical job and manufacturing computation system according to any of Clauses 1-11, wherein the lens design system, the lab management system, and the plurality of optical manufacturing equipment comprises software from multiple parties including a LDS vendor and an LMS vendor.

Clause 13. A computer-implemented method for modifying optical manufacturing data, the method comprising: receiving the optical manufacturing data associated with an optical job; and modifying the optical manufacturing data using manufacturing logic to generate modified optical manufacturing data.

Clause 14. The computer-implemented method of Clause 13, further comprising using the modified optical manufacturing data in the manufacturing of the optical job or communicating the modified optical manufacturing data to a lab equipment or LMS for use in the manufacturing of the optical job.

Clause 15. The computer-implemented method of Clauses 13-14, wherein modifying the optical manufacturing data using the manufacturing logic to generate modified optical manufacturing data is performed by at least one of a lab management system, a network device located on a lab server network, or by a lab equipment that uses the modified optical manufacturing data.

Clause 16. The computer-implemented method of Clauses 13-15, wherein the manufacturing logic comprises logic for at least one re-computing the optical manufacturing data for a different manufacturing process, a new lab equipment, a new measurement, a specific condition of a lab equipment, and/or subsequent equipment along the process line associated with the optical job.

Clause 17. The computer-implemented method of Clauses 13-16, wherein the manufacturing logic comprises logic for: 1) an optical lens blocker to recalculate blocking parameters for the optical job based on conditions of the optical lens blocker, 2) re-computing the optical manufacturing data for a different manufacturing process, and/or 3) calculating updated generating and engraving parameters based on a measurement of a position of a lens on a surfacing block.

Clause 18. A system comprising: memory configured to store computer executable instructions and data; a network interface configured to enable communication of data with at least one networked device; and a processor for executing the computer executable instructions, wherein the system is configured to store manufacturing logic.

Clause 19. The system according to Clause 18, where the system is at least one of a LDS, a LMS, a Rx lab network device, and a lab equipment.

Clause 20. The system according to Clause 18, where the system is a LDS and wherein the LDS is configured to determine optical manufacturing data in response to receiving an optical lens design request from a LMS; and communicate the optical manufacturing data and the manufacturing logic to the LMS.

Clause 21. The system according to Clause 20, wherein the optical manufacturing data is communicated separately from the manufacturing logic.

Clause 22. The system according to Clause 20, wherein the optical manufacturing data and the manufacturing logic are grouped together and communicated together in one or more data packets to the LMS.

Clause 23. The system according to Clause 18, where the system is a Rx lab network device and wherein the Rx lab network device is configured to use the manufacturing logic to modify optical manufacturing data for one or more Rx lab equipment.

What is claimed is:

1. A distributed optical job and manufacturing computation system comprising:
   a lens design system configured to receive an optical lens design request for an optical job;
   a lab management system in communication with the lens design system, the lab management system configured to send the optical lens design request to the lens design system, wherein the lens design system is configured to determine optical manufacturing data in response to the optical lens design request, and wherein the lens design system is configured to communicate the optical manufacturing data and manufacturing logic to the lab management system;
   a plurality of optical manufacturing equipment in communication with the lab management system, wherein the lab management system is configured to manage the workflow of optical jobs using the plurality of optical manufacturing equipment;
   wherein the lab management system is configured to associate at least optical manufacturing data to a manufacturing logic; and the manufacturing logic are configured to be notified as soon as the optical manufacturing data are updated, wherein a Job Computation Block (JCB) comprises logic (MCBs) and the optical manufacturing data being combined, wherein the JCB is configured to run the manufacturing logic code required to adjust the original data and configured to send the corrected data to the manufacturing equipment, the JCB is also configured to re-calculate any manufacturing data impacted by a change, wherein the JCB is configured to return then the updated manufacturing parameters for operation back to the manufacturing equipment, and wherein autonomous MCBs are configured to send update requests to the LDS to see if any new algorithm or update is released.

2. The distributed optical job and manufacturing computation system of claim 1, further comprising a lab network that includes at least one server, wherein the lab network is configured to communicate with the lab management system and the plurality of optical manufacturing equipment.

3. The distributed optical job and manufacturing computation system of claim 1, wherein the manufacturing logic is stored and executed at the lab management system.

4. The distributed optical job and manufacturing computation system of claim 2, wherein the manufacturing logic is stored and executed on the lab network.

5. The distributed optical job and manufacturing computation system of claim 1, wherein the manufacturing logic is stored and executed by at least one of the plurality of optical manufacturing equipment.

6. The distributed optical job and manufacturing computation system of claim 1, wherein the job computation block is deleted following a completion of the optical job.

7. The distributed optical job and manufacturing computation system of claim 1, wherein the manufacturing logic comprises logic that enables the modification of optical manufacturing data for a particular equipment along a process line associated with the optical job.

8. The distributed optical job and manufacturing computation system of claim 7, wherein the manufacturing logic comprises logic that also enables the modification of optical manufacturing data for subsequent equipment along the process line associated with the optical job.

9. The distributed optical job and manufacturing computation system of claim 8, wherein the manufacturing logic comprises logic for at least one of an optical lens blocker to recalculate blocking parameters for the optical job based on conditions of the optical lens blocker, re-computing the optical manufacturing data for a different manufacturing process, and calculating updated generating and engraving parameters based on a measurement of a position of a lens on a surfacing block.

10. A computer-implemented method for modifying optical manufacturing data, the method comprising:
receiving the optical manufacturing data associated with an optical job;
modifying the optical manufacturing data using distributed manufacturing logic to generate modified optical manufacturing data;
wherein a lab management system is configured to associate at least optical manufacturing data to a manufacturing logic; and
the manufacturing logic are configured to be notified as soon as the optical manufacturing data are updated,
wherein the optical job is associated with a Job Computation Block (JCB),
wherein the JCB comprises manufacturing logic (MCBs) and the optical manufacturing data being combined,
wherein the JCB is configured to run the logic code required to adjust the original data and configured to send the corrected data to the manufacturing equipment,
the JCB is also configured to re-calculate any manufacturing data impacted by a change,
wherein the JCB is configured to return then the updated manufacturing parameters for operation back to the manufacturing equipment, and
wherein autonomous MCBs are configured to send update requests to the LDS to see if any new algorithm or update is released.

11. The computer-implemented method of claim 10, further comprising using the modified optical manufacturing data in the manufacturing of the optical job.

12. The computer-implemented method of claim 10, wherein modifying the optical manufacturing data using the distributed manufacturing logic to generate modified optical manufacturing data is performed by a lab management system.

13. The computer-implemented method of claim 10, wherein the distributed manufacturing logic comprises logic for re-computing the optical manufacturing data for a different manufacturing process.

14. A lens design system (LDS) comprising:
memory configured to store computer executable instructions and data;
a network interface configured to enable the LDS to communicate data with at least one networked device; and
a processor for executing the computer executable instructions, wherein the computer executable instructions comprises instructions for:
determining optical manufacturing data in response to receiving an optical lens design request from a lab management system;
communicating the optical manufacturing data and manufacturing logic to the lab management system;
wherein the lab management system is configured to associate at least optical manufacturing data to a manufacturing logic; and
the manufacturing logic are configured to be notified as soon as the optical manufacturing data are updated,
wherein a Job Computation Block (JCB) comprises logic (MCBs) and the optical manufacturing data being combined,
wherein the JCB is configured to run the logic code required to adjust the original data and configured to send the corrected data to the manufacturing equipment,
the JCB is also configured to re-calculate any manufacturing data impacted by a change,
wherein the JCB is configured to return then the updated manufacturing parameters for operation back to the manufacturing equipment, and
wherein autonomous MCBs are configured to send update requests to the LDS to see if any new algorithm or update is released.

* * * * *